United States Patent [19]
Gordon et al.

[11] Patent Number: 4,885,114
[45] Date of Patent: Dec. 5, 1989

[54] METALLIZED TETRA((MESO)-5-METHYL-2-THIOPHENE)-PORPHINES, PLATINUM (5-BROMO OCTAETHYLPORPHINE) AND OPTICAL FILTERS CONTAINING SAME

[75] Inventors: Bruce S. Gordon, Shelton; Alan Adler, West Redding, both of Conn.

[73] Assignee: Barnes Engineering Co., Shelton, Conn.

[21] Appl. No.: 254,377

[22] Filed: Oct. 5, 1988

Related U.S. Application Data

[63] Continuation-in-part of Ser. No. 41,211, Apr. 22, 1987, abandoned.

[51] Int. Cl.$^4$ ................................................ F21V 9/06
[52] U.S. Cl. .................................... 252/589; 252/582; 350/311; 540/145
[58] Field of Search ............... 252/582, 589; 540/145; 350/311

[56] References Cited

U.S. PATENT DOCUMENTS

| | | | |
|---|---|---|---|
| 2,546,724 | 3/1951 | Coe ..................................... | 106/288 |
| 2,740,794 | 4/1956 | Bonner ............................... | 540/145 |
| 2,951,799 | 9/1960 | Sharp ................................. | 540/145 |
| 3,687,863 | 8/1972 | Wacher .............................. | 252/582 |
| 3,696,263 | 10/1972 | Wacher .............................. | 252/582 |
| 3,853,783 | 12/1974 | Tucker et al. ..................... | 252/582 |
| 4,622,174 | 11/1986 | McKoy et al. .................... | 252/582 |
| 4,663,084 | 5/1987 | Shirai et al. ....................... | 252/600 |

FOREIGN PATENT DOCUMENTS

| | | | |
|---|---|---|---|
| 62-061981 | 3/1987 | Japan ................................ | 540/145 |
| 1028672 | 7/1983 | U.S.S.R. ........................... | 540/145 |

OTHER PUBLICATIONS

Zanelli et al. "Synthetic Porphyrins as Tumor-Localizing Agents", Brit. Jour. Radiology, May 1981, pp. 403–407, vol. 54.

Primary Examiner—Howard J. Locker
Assistant Examiner—Catherine S. Kilby
Attorney, Agent, or Firm—Parmelee, Bollinger & Bramblett

[57] ABSTRACT

Transparent selective optical absorption filters of improved stability to ambient solar light and radiation in the near UV range are provided by incorporating metallized tetra ((meso)-5-methyl-2-thiophene) phorphines, platinum (5-bromo octaethylporphine) or mixtures thereof into suitable filter matrices such as plastic, glass or the like. Optical filters absorbing in narrow radiation bands and useful as transparent protective laser shields are provided.

38 Claims, No Drawings

METALLIZED TETRA((MESO)-5-METHYL-2-THIOPHENE)PORPHINES, PLATINUM (5-BROMO OCTAETHYLPORPHINE) AND OPTICAL FILTERS CONTAINING SAME

RELATED APPLICATION

This Application is a continuation-in-part of our earlier filed copending application Ser. No. 041,211 filed Apr. 22, 1987 now abandoned.

FIELD OF THE INVENTION

This invention relates to metallized tetra ((meso)-5-methyl-2-thiophene) porphines and platinum (5-bromo octaethylporphine) and selective optical absorption filters formed by incorporating said porphine derivatives in a suitable matrix. More particularly, this invention relates to a transparent protective laser shield device for protecting a viewer from damage by laser beam radiation.

BACKGROUND TO THE INVENTION

Selective optical absorption filters for selectively absorbing one or more narrow bands of radiation have found increasingly widespread use with the burgeoning use of lasers in the medical, industrial and scientific fields as well as in other fields. The increased use of various and multiple lasers has increased the possibility of the eye of a viewer or user of such lasers to be subject to dangerous exposure to the laser beam radiation and resulting in damage to the eye. Similarly, optical or light sensitive equipment employed for monitoring industrial or other operations being performed by lasers can also be subject to serious damage due to undesired or prolonged exposure to the radiation of the laser.

Thus, for such purposes, it is necessary to provide transparent optical filters or shields that can be interposed between the source of the radiation, e.g. the laser, and the viewer, e.g. the eye or other optical equipment, for specifically absorbing or filtering to a suitable degree one or more narrow bands of radiation while transmitting radiation to a suitable degree in a broader band surrounding or adjacent the narrow band.

In general such light source filters or shields, useful with various lasers, have been made available by incorporating a suitable light absorbing agent into a suitable matrix or host material. Such filters or shields enable the viewer to see through the transparent shield or filter but protects against damage to the viewer by exposure to undesired radiation from a laser beam. For example, in U.S. Pat. No. 3,853,783, issued Dec. 10, 1984 to Robert Tucker, it is disclosed that a vanadyl phthalocyanine sulfonamide may be incorporated into plastics to provide shields capable of protecting eyes against laser radiation of from about 620 to 720 nanometers. Similarly, in U.S. Pat. No. 3,687,863, issued Aug. 29, 1972 to Paul Wacker, it is disclosed that optical filters may be produced by incorporating metal derivatives of tetraphenylporphines into polymeric matrices. More recently, in U.S. Pat. No. 4,622,174, issued Nov. 11, 1986 to V. McKoy et al, it is disclosed that platinum octaethylporphine can be incorporated in a transparent matrix to absorb laser radiation at 532 nanometers or combined with a vanadyl phthalocyanine for absorption at both 532 and 694 nanometers.

However, many of the previously used absorbing agents produce optical filters of severely limited stability that results in an undesirable loss of optical density. Furthermore, it is found that many of the previously used absorbing agents do not provide sufficiently sharp absorption limits and possess undesirably broad absorption bands. Especially when two or more of such absorption agents are used in combination to protect a viewer against two or more wavelengths of radiation does the undesirable broad absorption bands of the agents represent a significant disadvantage, undesirably limiting transmission of other light available for vision.

Additionally, many of such absorbing agents are insufficiently stable to heat or in-band visible light radiation.

It is therefore highly desirable that absorbing agents be available which overcome one or more of these undesirable side effects and disadvantages of prior absorbing agents and optical filters produced therefrom. It is most desirable that absorbing agents be available for incorporation into suitable matrices for producing optical filters which have sharp narrow bands of absorption and are more stable to heat and in-band visible light. It is also highly desirable to have such absorption materials which can be combined with other absorption materials in suitable matrices for producing optical filters for suitably protecting viewers against two or more wavelengths of laser light.

SUMMARY OF THE INVENTION

Narrow band absorption agents which are suitably stable to heat and visible light are provided by platinum (5-bromo octaethylporphine) of the formula:

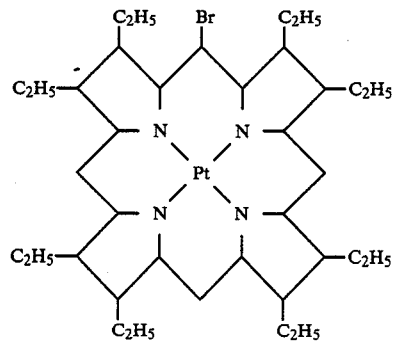

and metallized tetra ((meso)-5-methyl-2-thiophene) porphines of the formula

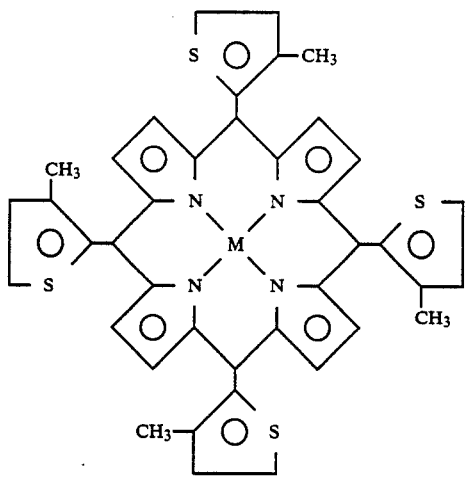

and the corresponding rotational isomers thereof wherein M is metal selected from the group consisting of nickel, palladium, rhodium, platinum, copper, silver, magnesium, indium, zinc, cobalt and iron. Especially preferred is the palladium derivative which has a sharp absorption band at about 531 nanometers and is especially useful for producing an optical filter for use with a double YAG (neodynium) laser.

The porphine derivatives of this invention are characterized by a strong absorption band in the visible spectrum region, generally a strong narrow absorption band somewhere in the wavelength range of from about 520 to 555 nanometers. The wavelengths of the narrow absorption band will depend upon the metal M of the metallized tetra ((meso)-5-methyl-2-thiophene) porphine derivatives. Selecting a suitable metal provides a degree of selectivity to place the absorption band in any of various desired locations within the spectral band. Platinum (5-bromo octaethylporphine) has peak absorption bands at 521 and 554 nanometers.

Transparent optical laser filters or shields are prepared by incorporating a suitable light absorbing effective amount of these metallized tetra ((meso)-5-methyl-2-thiophene) porphine derivatives, platinum (5-bromo octaethylporphine) or mixtures thereof alone or combined with other suitable absorbing agents in a suitable host material such as amorphous or crystalline transparent glass or plastic material or suspended in a suitable liquid between two transparent glass or plastic plates. Such optical filters or shields can then be interposed between a laser beam and the eye or device of a viewer for adjustably absorbing one or more of the narrow band radiations while transmitting in a broader band surrounding or adjacent to the narrow band wavelengths.

DETAILS OF THE INVENTION

The metallized tetra ((meso)-5-methyl-2-thiophene) porphine derivatives of this invention are readily prepared b reacting tetra ((meso)-5-methyl-2-thiophene) porphine free base with an appropriate metal adduct, such as a metal halide, preferably metal chloride, in a suitable reaction solvent. For example, the palladium derivative of tetra ((meso)-5-methyl-2-thiophene) porphine may be prepared by reacting the porphine free base with palladium chloride in dimethyl formamide. Similarly, platinum (5-bromo octaethylporphine) is readily prepared by reacting 5-bromo octaethylporphine with an appropriate platinum adduct, such as a platinum halide, preferably platinum chloride, in a suitable reaction solvent, such as, for example, in dimethyl formamide.

The protective optical shields or filters of this invention are formed by incorporating in a transparent host material having substantial transmission properties of optical radiation over a selected broad range of wavelengths a chromophore which is platinum (5-bromo octaethylporphine), a metallized tetra ((meso)-5-methyl-2-thiophene) porphine or mixtures thereof as hereinbefore described and which absorbs optical radiation at predetermined narrow band widths located within the broad band wavelength which is passed by the host material. Such shields or filters protect the viewer from the laser beam by absorption of a substantial portion of the laser beam before it reaches the viewer while still permitting the viewer to see the laser beam environment.

It will be recognized that the viewer may be either the human eye of an individual or any of the various forms of radiation sensitive detectors such as a photomultiplier tube, photodetector, image tube, camera tube, image intensifier, vidicon and the like which views a scene and is desired to be protected from a narrow band laser beam which is focused or otherwise gathered or collected by an optical system and applied to the detector or human eye.

The optical filter or shield may be in any suitable form, such as for example, a protective window, shield, plate, visor, goggles or as an absorption medium suspended between two transmitting plates, and intended to prevent injury to the viewer.

The absorbing agents of this invention may be incorporated in a suitable host material such as crystal, glass, plastic or polycrystalline material or suspended in liquid form between two transparent plates, such as glass or plastic plates to form an optical filter or shield which can be in the form of a window, visor, shield or goggles as previously mentioned. Incorporation of the absorbing agent into host material can be by any suitable means, such as for example, by simply mixing the absorbing agent and host material in a ball mill or mixing the absorbing agent and host material in a suitable solvent, before forming the host material into an article such as by extrusion or compression molding or the like in order to provide a homogeneous dispersion of absorbing agent in host material.

Preferably, however, the absorbing agents are incorporated into the host material by diffusing a layer of the absorbing agent into the surface of the matrix material after the host material has already been suitably formed into an article. Diffusion into the host material can be accomplished, for example, by the method disclosed in co-pending U.S. patent application Ser. No. 710,148, filed Mar. 11, 1985, now U.S. Pat. No. 4,657,345, of Bruce S. Gordon, which Application is incorporated herein by reference thereto. Using these or similar methods, an absorbing effective amount of the absorbing agent is incorporated into the host material and diffused into the surface layer of a host material article sufficient to enable optical shields or filters to be formed therefrom. Generally, an absorbing effective amount of the absorbing agents of this invention incorporated into the host material, such as an optical part 0.080 inches thick made of 1.2 grams/cm³ polycarbonate, will be from about 100 to about 2000 parts by weight of absorbing agent per million parts by weight of host material or if diffused into a surface layer of a host material article will be an amount sufficient to provide density of from about $2.10-5$ to about $2.10-4$ grams/cm$^2$ of absorbing agents on the surface of the host material.

As examples of suitable host materials there may be mentioned glass and thermoplastic polymeric materials such as acrylate and methacrylate polymers, polycarbonates, polyvinyl chlorides, polystyrene and the like, particularly polymethyl methacrylates and polycarbonates.

It is often most desirable to provide optical shields or filters which provide absorption at two or more separate laser band widths within the range of wavelengths from 350 to 1400 nanometers. For this purpose, the previously described absorbing agents of this invention can be combined with one or more other absorbing agents. As examples of other known absorbing agents with which the absorbing agents of this invention may be combined there can be mentioned, for example, t-butylated vanadyl phthalocyanine, tris(p-dialkylaminophenyl)aminium hexafluoroantimonates or -arsenates such as disclosed in U.S. Pat. No. 3,440,257, especially such tris(p-dialkylaminophenyl)-aminium hexafluoroantimonate or -arsenate available from American Cyanamid Company as IR-282, bis(p-dialkylaminophenyl) [N,N-bis(p-dialkylaminophenyl)-p-aminophenyl-]aminium salts, especially bis(p-diethylaminophenyl)[N,N-bis(p-diethylaminophenyl)-p-aminophenyl]aminium hexafluoroantimonate, disclosed in U.S. Patent 3,484,467, 5,5,-dichloro-11-diphenylamine-3,3,-diethyl-10,12-ethylenethiatricarbocyanine perchlorate available from Eastman Kodak Co. as IR-140 and thiopyrillium dye 26, having the structure disclosed at page 206 of Optics Letter, Vol. 8, No. 4, April 1983 and available from Eastman Kodak Co. It is especially preferred that. palladium tetra ((meso)-5-methyl-2-thiophene) porphine absorbing at 531 nanometers be employed in combination with t-butylated vanadyl phthalocyanine since the combination provides optical filters or shields with even greater stability, clarity and freedom from haze upon repeated absorption at 532 nanometers than when using palladium tetra ((meso)-5-methyl-2-thiophene) porphine alone in such an optical shield or filter.

Although not required it is preferred that the optical filters or shields containing the novel absorbing agents of this invention be provided with a protective transparent coating containing an ultraviolet absorbing agent effective for absorbing radiation below about 450 nanometers to provide additional stability to the optical filter or shield. As an example of a suitable and preferred UV absorbing agent that may be incorporated into such a transparent coating that may be deposited on the surface of an optical filter or shield of this invention, there may be mentioned the dye identified on the Color Index as Yellow Disperse 201, sold under the name Macrolex 6G by Mobay Corporation, Pittsburgh, Pa.

The invention is illustrated by but not limited to the following examples.

EXAMPLE 1

Preparation of Palladium tetra ((meso)-5-methyl-2-thiophene) porphine

In a suitable 150 ml vessel 50 ml of dimethylformamide is brought to reflux and 20 mg tetra ((meso)-5-methyl-2-thiophene) porphine free base is added and dissolved. To this solution 5 mg palladium chloride is added and permitted to react for about 20 minutes. Thereafter, the reaction mixture is permitted to cool and crystal formation promoted by the addition of 50 ml distilled water. The reaction mixture is allowed to sit for about twenty four hours to facilitate separation of the solid phase. The reaction mixture is filtered by vacuum filtration and the solids retained.

The solid product is purified using a $1\frac{1}{4} \times 14''$ ($3.18 \times 35.56$ cm) chromatography column. In the bottom of the column a small amount of glass wool is placed and above this about $\frac{3}{4}''$ (1.9 cm) of clear insoluble silicate sand followed by about $12''$ (30.48 cm) of Brockman #1 acid alumina and the column packed down to about $9''$ to $10''$ (24.13 to 25.4 cm) to remove any gulleys. Thereafter, another $\frac{3}{4}''$ (1.9 cm) layer of insoluble silicate sand is placed on top of the column. A dry column is employed and the separated solid material from the above reaction is washed into the column using chloroform and the column filled with chloroform after all the solids are in the column and absorbed into the upper sand layer. The layers are visible to the eye and fractions are collected at the bottom of the column and checked for consistency and purity by a spectrophotometer. About 16 mg of the desired product are obtained.

EXAMPLE 2

In a manner similar to that described in Example 1, the corresponding nickel, rhodium, platinum, copper, silver, magnesium, indium, zinc, cobalt and iron derivatives of tetra ((meso)-5-methyl-2-thiophene) porphine can be prepared by substitution of the appropriate amount of the corresponding metal chloride for palladium chloride.

EXAMPLE 3

Preparation of Platinum (5-Bromo Octaethylporphine)

In a suitable 150 ml vessel 50 ml of dimethylformamide is brought to reflux and 20 mg 5-bromo octaethylporphine free base is added and dissolved. To this solution 8 mg platinum chloride is added and permitted to react for about 20 minutes. Thereafter, the reaction mixture is permitted to cool and crystal formation promoted by the addition of 50 ml distilled water. The reaction mixture is allowed to sit for about twenty four hours to increase crystal size. The reaction mixture is filtered by vacuum filtration and the solids retained.

The solid product is purified using a $1\frac{1}{4} \times 14''$ chromatography column. In the bottom of the column a small amount of glass wool is placed and above this about $\frac{3}{4}''$ of clear OTTOWA SAND followed by about $12''$ of Brockman #1 acid alumina and the column packed down to about $9\frac{1}{2}$ to $10''$ to remove any gulleys. Thereafter, another $\frac{3}{4}''$ layer of OTTOWA SAND is placed on top of the column. The column is run dry and the separated solid material from the above reaction is washed into the column using chloroform and the column filled with chloroform after all the solids are in the column and absorbed into the upper sand layer. The layers are visible to the eye and fractions are collected at the bottom of the column and checked for consistency and purity by a spectrophotometer. About 16 mg of the desired product are obtained.

EXAMPLE 4

Laser shields of this invention are prepared by diffusing a light absorbing effective amount of the palladium tetra ((meso)-5-methyl-2-thiophene) porphine of Example 1 or platinum (5-bromo octaethylporphine) of Example 3 into at least one surface of polymethyl methacrylate and polycarbonate matrices in accordance with the process described in the aforesaid U.S. Pat. No. 4,657,345.

The laser shields preferably have a combination of a light absorbing agent of this invention along with other light absorbing agents incorporated into the polymeric matrices. As examples of such combinations of absorbing agents incorporated into matrices to produce laser shields of this invention, there may be mentioned for example the following combination:

(A) palladium tetra ((meso)-5-methyl-2-thiophene) porphine and t-butylated vanadyl phthalocyanine;

(B) palladium tetra ((meso)-5-methyl-2-thiophene) porphine and a tris(p-dialkylaminophenyl)aminium hexafluoroantimonate;

(C) palladium tetra ((meso)-5-methyl-2-thiophene) porphine and a tris(p-dialkylaminophenyl)aminium hexafluoroarsenate;

(D) palladium tetra ((meso)-5-methyl-2-thiophene) porphine and thiopyrillium dye 26;

(E) palladium tetra ((meso)-5-methyl-2-thiophene) porphine and 5,5'-dichloro-11-diphenylamine-3,3'-diethyl-10,12-ethylenethiatricarbocyanine perchlorate;

(F) palladium tetra ((meso)-5-methyl-2-thiophene) porphine and bis(p-diethylaminophenyl)[N,N-bis(p-diethylaminophenyl)-p-aminophenyl]aminium hexafluoroantimonate;

(G) palladium tetra ((meso)-5-methyl-2-thiophene) porphine, t-butylated vanadyl phthalocyanine and a tris(p-dialkylaminophenyl)aminium hexafluoroantimonate;

(H) palladium tetra ((meso)-5-methyl-2-thiophene) porphine, t-butylated vanadyl phthalocyanine and a tris(p-dialkylaminophenyl)aminium hexafluoroarsenate;

(I) palladium tetra ((meso)-5-methyl-2-thiophene) porphine, t-butylated vanadyl phthalocyanine and thiopyrillium dye 26;

(J) palladium tetra ((meso)-5-methyl-2-thiophene) porphine, t-butylated vanadyl phthalocyanine and 5,5'-dichloro-11-diphenylamine-3,3'-diethyl-10,12-ethylenethiatricarbocyanine perchlorate;

(K) palladium tetra ((meso)-5-methyl-2-thiophene) porphine, t-butylated vanadyl phthalocyanine and bis(p-diethylaminophenyl)[N,N-bis(p-diethylaminophenyl)-p-aminophenyl]aminium hexafluoroantimonate;

(L) palladium tetra ((meso)-5-methyl-2-thiophene) porphine, t-butylated vanadyl phthalocyanine, tris(p-diethylaminophenyl)aminium hexafluoroantimonate and 5,5'-dichloro-11-diphenylamine-3,3'-diethyl-10,12-ethylenethiatricarbocyanine perchlorate;

(M) palladium tetra ((meso)-5-methyl-2-thiophene) porphine, t-butylated vanadyl phthalocyanine, tris(p-diethylaminophenyl)aminium hexafluoroarsenate and 5,5,-dichloro-11-diphenylamine-3,3,-diethyl-10,12-ethylenethiatricarbocyanine perchlorate;

(N) palladium tetra ((meso)-5-methyl-2-thiophene) porphine, t-butylated vanadyl phthalocyanine, thiopyrillium dye 26 and 5,5'-dichloro-11-diphenylamine-3,3'-diethyl -10,12- ethylenethiatricarbocyanine perchlorate;

(O) palladium tetra ((meso)-5-methyl-2-thiophene) porphine, t-butylated vanadyl phthalocyanine, bis(p-diethylaminophenyl)[N,N-bis(p-diethylaminophenyl)-p-aminophenyl]aminium hexafluoroantimonate and 5,5'-dichloro-11-diphenylamine-3,3'-diethyl-10,12-ethylenethiatricarbocyanine perchlorate;

(P) platinum (5-bromo octaethylporphine) and t-butylated vanadyl phthalocyanine;

(Q) platinum (5-bromo octaethylporphine) and a tris(p-dialkylaminophenyl)aminium hexafluoroantimonate;

(R) platinum (5-bromo octaethylporphine) and a tris(p-dialkylaminophenyl)aminium hexafluoroarsenate;

(S) platinum (5-bromo octaethylporphine) and thiopyrillium dye 26;

(T) platinum (5-bromo octaethylporphine) and 5,5'-dichloro-11-diphenylamine-3,3'-diethyl-10,12-ethylenethiatricarbocyanine perchlorate;

(U) platinum (5-bromo octaethylporphine) and bis(p-diethylaminophenyl)[N,N-bis(p-diethylaminophenyl)-p-aminophenyl]aminium hexafluoroantimonate;

(V) platinum (5-bromo octaethylporphine), palladium tetra ((meso)-5-methyl-2-thiophene) porphine and t-butylated vanadyl phthalocyanine;

(W) platinum (5-bromo octaethylporphine), palladium tetra ((meso)-5-methyl-2-thiophene) porphine and a tris(p-dialkylaminophenyl)aminium hexafluoroantimonate;

(X) platinum (5-bromo octaethylporphine), palladium tetra ((meso)-5-methyl-2-thiophene) porphine and a tris(p-dialkylaminophenyl)aminium hexafluoroarsenate;

(Y) platinum (5-bromo octaethylporphine), palladium tetra ((meso)-5-methyl-2-thiophene) porphine and thiopyrillium dye 26;

(Z) platinum (5-bromo octaethylporphine), palladium tetra ((meso)-5-methyl-2-thiophene) porphine and 5,5'-dichloro-11-diphenylamine-3,3'-diethyl-10,12-ethylenethiatricarbocyanine perchlorate;

(AA) platinum (5-bromo octaethylporphine), palladium tetra ((meso)-5-methyl-2-thiophene) porphine and bis(p-diethylaminophenyl)[N,N-bis(p-diethylaminophenyl)-p-aminophenyl]aminium hexafluoroantimonate;

(BB) platinum (5-bromo octaethylporphine), palladium tetra ((meso)-5-methyl-2-thiophene) porphine, t-butylated vanadyl phthalocyanine and a tris(p-dialkylaminophenyl)aminium hexafluoroantimonate;

(CC) platinum (5-bromo octaethylporphine), palladium tetra ((meso)-5-methyl-2-thiophene) porphine, t-butylated vanadyl phthalocyanine and a tris(p-dialkylaminophenyl)aminium hexafluoroarsenate;

(DD) platinum (5-bromo octaethylporphine), palladium tetra ((meso)-5-methyl-2-thiophene) porphine, t-butylated vanadyl phthalocyanine and thiopyrillium dye 26;

(EE) platinum (5-bromo octaethylporphine), palladium tetra ((meso)-5-methyl-2-thiophene) porphine, t-butylated vanadyl phthalocyanine and 5,5'-dichloro-11-diphenylamine-3,3'-diethyl-10,12ethylenethiatricarbocyanine perchlorate;

(FF) platinum (5-bromo octaethylporphine), palladium tetra ((meso)-5-methyl-2-thiophene) porphine, t-butylated vanadyl phthalocyanine and bis(p-diethylaminophenyl)[N,N-bis(p-diethylaminophenyl)-p-aminophenyl]aminium hexafluoroantimonate;

(GG) platinum (5-bromo octaethylporphine), palladium tetra ((meso)-5-methyl-2-thiophene) porphine, t-butylated vanadyl phthalocyanine, tris(p-diethylaminophenyl)aminium hexafluoroantimonate and 5,5'-dichloro-11-diphenylamine-3,3'-diethyl-10,12ethylenethiatricarbocyanine perchlorate;

(HH) platinum (5-bromo octaethylporphine), palladium tetra ((meso)-5-methyl-2-thiophene) porphine, t-butylated vanadyl phthalocyanine, tris(p-diethylaminophenyl)aminium hexafluoroarsenate and 5,5'-dichloro-11-diphenylamine-3,3'-diethyl-10,12ethylenethiatricarbocyanine perchlorate;

(II) platinum (5-bromo octaethylporphine), palladium tetra ((meso)-5-methyl-2-thiophene) porphine, t-butylated vanadyl phthalocyanine, thiopyrillium dye 26 and 5,5'-dichloro-11-diphenylamine-3,3'-diethyl-10,12- ethylenethiatricarbocyanine perchlorate;

(JJ) platinum (5-bromo octaethylporphine), palladium tetra ((meso)-5-methyl-2-thiophene) porphine, t-butylated vanadyl phthalocyanine, bis(p-diethylaminophenyl)[N,N-bis(p-diethylaminophenyl)-p-aminophenyl]aminium hexafluoroantimonate and 5,5'-dichloro-11-diphenylamine-3,3'-diethyl-10,12-ethylenethiatricarbocyanine perchlorate;

In another preferred aspect of this invention laser shields having any of the hereinbefore absorbing agents or combination of absorbing agents incorporated therein are provided with a hard clear protective UV absorbing coating, particularly a coating containing Yellow Disperse 201 (Macrolex 6G) from Mobay Corporation.

Since other changes and modifications varied to fit particular operating requirements and environments will be apparent to those skilled in the art, the invention is not considered limited to the examples chosen for purposes of illustration, and includes all changes and modifications which do not constitute a departure from the true spirit and scope of this invention as claimed in the following claims and equivalents thereto.

What is claimed is:

1. A metallized tetra ((meso)-5-methyl-2-thiophene) porphine of the formula:

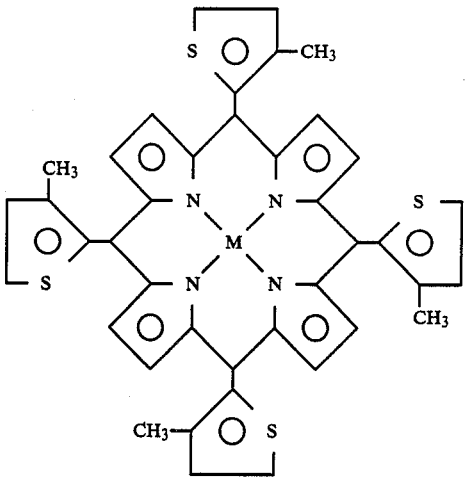

and the corresponding rotational isomers thereof wherein M is metal selected from the group consisting of nickel, palladium, rhodium, platinum, copper, silver, magnesium, indium, zinc, cobalt and iron.

2. A metallized tetra ((meso)-5-methyl-2-thiophene) porphine of claim 1 which is palladium tetra ((meso)-5-methyl-2-thiophene) porphine.

3. A transparent optical filter or shield adapted to be interposed between a source of radiation and a viewer for absorbing a narrow band of radiation while transmitting optical radiation within a broader wavelength band which includes the narrow band radiation for protecting a viewer comprising a matrix material substantially transparent to visible light containing a light absorbing effective amount of a metallized tetra ((meso)-5-methyl-2-thiophene) porphine of the formula:

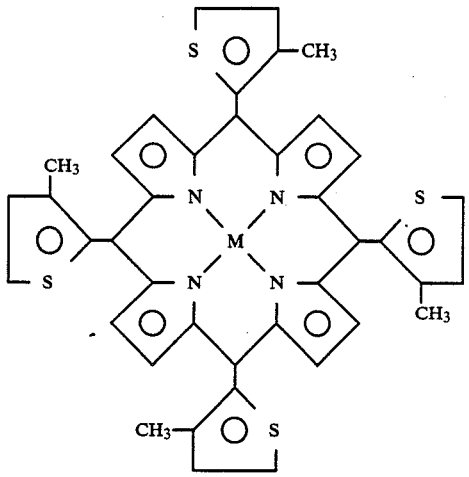

and the corresponding rotational isomers thereof wherein M is metal selected from the group consisting of nickel, palladium, rhodium, platinum, copper, silver, magnesium, indium, zinc, cobalt and iron.

4. A transparent optical filter or shield of claim 3 wherein the metallized tetra ((meso)-5-methyl-2-thiophene) porphine is palladium tetra ((meso)-5-methyl-2-thiophene) porphine.

5. A transparent optical filter or shield of claim 3 for absorbing narrow band laser beam radiation.

6. A transparent optical filter or shield of claim 4 for absorbing narrow band laser beam radiation.

7. A transparent optical filter or shield of claim 5 wherein the matrix material is a polymeric plastic.

8. A transparent optical filter or shield of claim 6 wherein the matrix material is a polymeric plastic.

9. A transparent optical filter or shield of claim 8 wherein the matrix also has incorporated therein a light absorbing effective amount of one or more additional optical absorbing agents selected from the group consisting of a t-butylated vanadyl phthalocyanine, a tris(p-dialkylaminophenyl)aminium hexafluoroantimonate, a tris(p-dialkylaminophenyl)aminium hexafluoroarsenate, a bis(p-dialkylaminophenyl)[N,N-bis(p-dialkylaminophenyl)-p-aminophenyl]aminium salt, 5,5'-dichloro-11-diphenylamine-3,3,'-diethyl-10,12-ethylenethiatricarbocyanine perchlorate and thiopyrillium dye 26.

10. A transparent optical filter or shield of claim 9 wherein t-butylated vanadyl phthalocyanine is present in the plastic matrix.

11. A transparent optical filter or shield of claim 9 wherein a tris(p-dialkylaminophenyl)aminium hexafluoroantimonate is present in the plastic matrix.

12. A transparent optical filter or shield of claim 9 wherein a tris(p-dialkylaminophenyl)aminium hexafluoroarsenate is present in the plastic matrix.

13. A transparent optical filter or shield of claim 9 wherein thiopyrillium dye 26 is present in the plastic matrix.

14. A transparent optical filter or shield of claim 9 wherein 5,5'-dichloro-11-diphenylamine-3,3'-diethyl-10,12-ethylenethiatricarbocyanine perchlorate is present in the plastic matrix.

15. A transparent optical filter or shield of claim 9 wherein bis(p-diethylaminophenyl)[N,N-(p-diethylaminophenyl)-p-aminophenyl]aminium hexafluoroantimonate is present in the plastic matrix.

16. A transparent optical filter or shield of claim 9 wherein t-butylated vanadyl phthalocyanine and a tris(p-dialkylaminophenyl)aminium hexafluoroantimonate are present in the plastic matrix.

17. A transparent optical filter or shield of claim 9 wherein t-butylated vanadyl phthalocyanine and a tris(p-dialkylaminophenyl)aminium hexafluoroarsenate are present in the plastic matrix.

18. A transparent optical filter or shield of claim 9 wherein t-butylated vanadyl phthalocyanine and thiopyrillium dye 26 are present in the plastic matrix.

19. A transparent optical filter or shield of claim 9 wherein t-butylated vanadyl phthalocyanine and 5,5'-dichloro-11-diphenylamine-3,3'-diethyl-10,12-ethylenethiatricarbocyanine perchlorate are present in the plastic matrix.

20. A transparent optical filter or shield of claim 9 wherein t-butylated vanadyl phthalocyanine and bis(p-diethylaminophenyl)[N,N-bis(p-diethylaminophenyl)-p-aminophenyl]aminium hexafluoroantimonate are present in the plastic matrix.

21. A transparent optical filter or shield of claim 9 wherein t-butylated vanadyl phthalocyanine, a tris(p-dialkylaminophenyl)aminium hexafluoroarsenate and 5,5'-dichloro-11-diphenylamine-3,3'-diethyl-10,12-ethylenethiatricarbocyanine perchlorate are present in the plastic matrix.

22. A transparent optical filter or shield of claim 9 wherein t-butylated vanadyl phthalocyanine, 5,5'-dichloro-11-diphenylamine-3,3'-diethyl-10,12-ethylenethiatricarbocyanine perchlorate and thiopyrillium dye 26 are present in the plastic matrix.

23. A transparent optical filter or shield of claim 9 wherein t-butylated vanadyl phthalocyanine, 5,5'-dichloro-11-diphenylamine-3,3'-diethyl-10,12-ethylenethiatricarbocyanine perchlorate and a tris(p-dialkylaminophenyl)aminium hexafluoroantimonate are present in the plastic matrix.

24. A transparent optical filter or shield of claim 9 wherein t-butylated vanadyl phthalocyanine, 5,5'-dichloro-11-diphenylamine-3,3'-diethyl-10,12-ethylenethiatricarbocyanine perchlorate and bis(p-diethylaminophenyl)[N,N-bis(p-diethylaminophenyl)-p-aminophenyl]aminium hexafluoroantimonate are present in the plastic matrix.

25. A transparent optical filter or shield of claim 7 wherein the matrix is coated with a transparent UV absorbing coating.

26. A transparent optical filter or shield of claim 8 wherein the matrix is coated with a transparent UV absorbing coating.

27. A transparent optical filter or shield of claim 9 wherein the matrix is coated with a transparent UV absorbing coating.

28. A transparent optical filter or shield of claim 15 wherein the matrix is coated with a transparent UV absorbing coating.

29. A transparent optical filter or shield of claim 25 wherein the UV absorbing coating contains Yellow Disperse 201.

30. A transparent optical filter or shield of claim 26 wherein the UV absorbing coating contains Yellow Disperse 201.

31. A transparent optical filter or shield of claim 27 wherein the UV absorbing coating contains Yellow Disperse 201.

32. A transparent optical filter or shield of claim 28 wherein the UV absorbing coating contains Yellow Disperse 201.

33. A transparent optical filter or shield of claim 3 wherein the matrix also has incorporated therein a light absorbing effective amount of platinum (5-bromo octaethylporphine).

34. A transparent optical filter or shield of claim 33 wherein the matrix also has incorporated therein a light absorbing effective amount of one or more additional optical absorbing agents selected from the group consisting of a t-butylated vanadyl phthalocyanine, a tris(p-dialkylaminophenyl)aminium hexafluoroantimonate, a tris(p-dialkylaminophenyl)aminium hexafluoroarsenate, a bis(p-dialkylaminophenyl)[N,N-bis(p-dialkylaminophenyl)-p-aminophenyl]aminium salt, 5,5'-dichloro-11-diphenylamine-3,3'-diethyl-10,12-ethylenethitricarbocyanine perchlorate and thiopyrillium dye 26.

35. A transparent optical filter or shield of claim 33 wherein the matrix is coated with a transparent UV absorbing coating.

36. A transparent optical filter or shield of claim 34 wherein the matrix is coated with a transparent UV absorbing coating.

37. A transparent optical filter or shield of claim 35 wherein the UV absorbing coating contains Yellow Disperse 201.

38. A transparent optical filter or shield of claim 36 wherein the UV absorbing coating contains Yellow Disperse 201.

* * * * *